(12) United States Patent
Mouchawar et al.

(10) Patent No.: US 10,686,228 B2
(45) Date of Patent: Jun. 16, 2020

(54) POUCH BATTERY FOR USE IN IMPLANTABLE ELECTRONIC DEVICES

(71) Applicant: Pacesetter, Inc., Santa Clara, CA (US)

(72) Inventors: Gabriel A. Mouchawar, Valencia, CA (US); Russell Bruch, Seneca, SC (US)

(73) Assignee: Pacesetter, Inc., Santa Clara, CA (US)

( * ) Notice: Subject to any disclaimer, the term of this patent is extended or adjusted under 35 U.S.C. 154(b) by 133 days.

(21) Appl. No.: 15/842,747

(22) Filed: Dec. 14, 2017

(65) Prior Publication Data

US 2018/0166747 A1 Jun. 14, 2018

Related U.S. Application Data

(60) Provisional application No. 62/434,217, filed on Dec. 14, 2016.

(51) Int. Cl.
| | |
|---|---|
| *H01M 10/42* | (2006.01) |
| *A61N 1/378* | (2006.01) |
| *H01M 2/10* | (2006.01) |
| *H01M 2/02* | (2006.01) |
| *A61N 1/375* | (2006.01) |

(52) U.S. Cl.
CPC .......... *H01M 10/425* (2013.01); *A61N 1/375* (2013.01); *A61N 1/378* (2013.01); *A61N 1/3787* (2013.01); *A61N 1/37512* (2017.08); *H01M 2/026* (2013.01); *H01M 2/0207* (2013.01); *H01M 2/0287* (2013.01); *H01M 2/1055* (2013.01); *H01M 2/1061* (2013.01); *H01M 10/4235* (2013.01); *H01M 2220/30* (2013.01); *H01M 2300/0025* (2013.01)

(58) Field of Classification Search
CPC . H01M 10/425; A61N 1/375; A61N 1/37512; A61N 1/378
USPC ........................................................ 429/127
See application file for complete search history.

(56) References Cited

U.S. PATENT DOCUMENTS

| | | | | |
|---|---|---|---|---|
| 5,747,192 | A * | 5/1998 | Hughen | G09F 3/04 |
| | | | | 429/163 |
| 6,042,966 | A | 3/2000 | Cheu | |
| 6,498,951 | B1 * | 12/2002 | Larson | A61N 1/375 |
| | | | | 607/36 |

(Continued)

FOREIGN PATENT DOCUMENTS

EP 2648259 A2 10/2013

OTHER PUBLICATIONS

Srinivasulu, et al., "An Engineering Perspective of External Cardiac Loop Recorder: A Systematic Review," 2016, Journal of Medical Engineering, Hindawi Publishing Corporation, vol. 2016, 16 pages.

*Primary Examiner* — James M Erwin

(57) ABSTRACT

Disclosed herein is a battery with a pouch-type enclosure for use with an implantable electronic device. The battery may have greater than 20 megaohms of isolation between the anode and the external surface of the pouch-type battery enclosure and the cathode and the external surface of the pouch-type battery enclosure. The battery may have a pouch-type enclosure with a contoured shape, including a cathode, anode, and electrolyte disposed within the pouch-type enclosure. The cathode and/or anode may have variable thicknesses. The variable thickness anode and/or cathode may be contoured in shape to at least partially provide the contoured shape of the pouch-type enclosure.

20 Claims, 5 Drawing Sheets

(56) References Cited

U.S. PATENT DOCUMENTS

| | | |
|---|---|---|
| 8,433,409 B2 | 4/2013 | Johnson et al. |
| 9,325,029 B1 * | 4/2016 | Chul .................. H01M 6/46 |
| 9,825,334 B2 | 11/2017 | Kim et al. |
| 2002/0127362 A1 | 9/2002 | Jansen et al. |
| 2007/0072071 A1 | 3/2007 | Lee |
| 2007/0154794 A1 | 7/2007 | Kim et al. |
| 2012/0040235 A1 | 2/2012 | Cho et al. |
| 2013/0196214 A1 * | 8/2013 | Scott .................. H01M 2/022 |
| | | 429/174 |
| 2013/0302668 A1 | 11/2013 | Lim et al. |
| 2016/0056416 A1 | 2/2016 | Flitsch et al. |
| 2016/0315302 A1 | 10/2016 | Aamodt et al. |

* cited by examiner

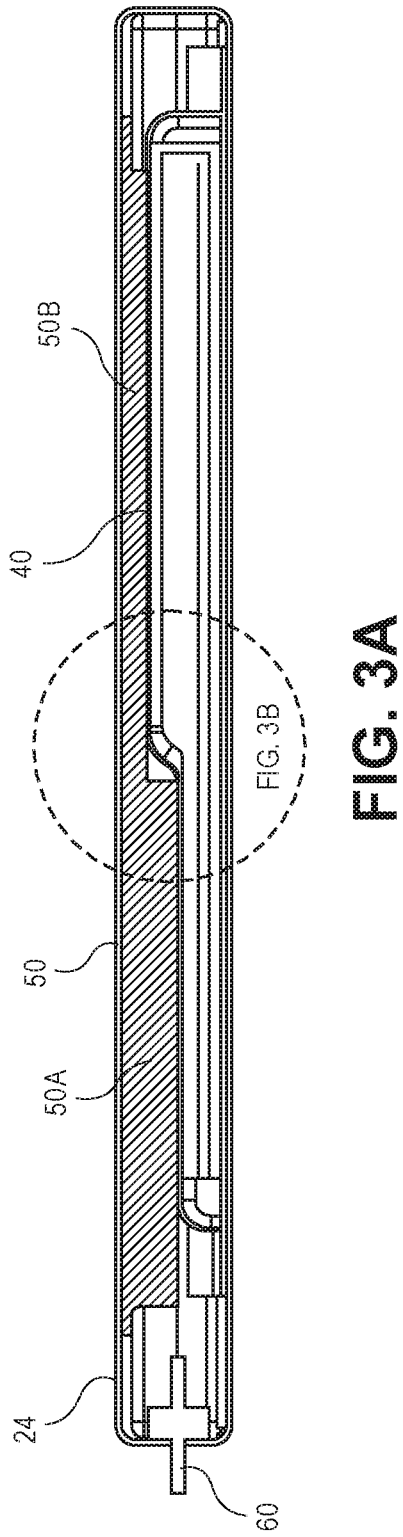
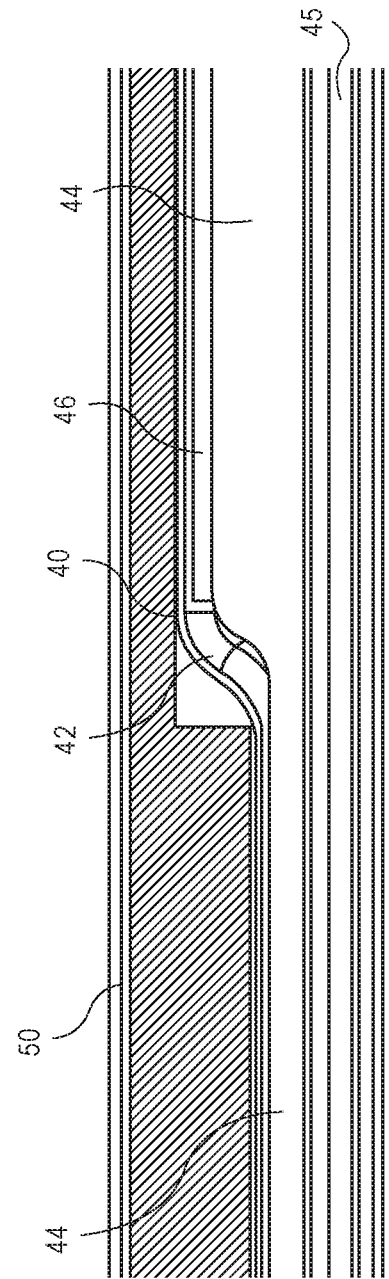
FIG. 3A
FIG. 3B

POUCH BATTERY FOR USE IN IMPLANTABLE ELECTRONIC DEVICES

PRIORITY

This application claims the benefit of U.S. Provisional Application No. 62/434,217, filed Dec. 14, 2016.

FIELD OF THE INVENTION

Embodiments herein generally relate to implantable electronic devices, and more particularly to implantable medical devices having a pouch battery, related devices and methods of manufacture.

BACKGROUND OF THE INVENTION

Implantable electronic devices (IEDs) include implantable cardiac monitoring (ICM) devices (or loop recorders) used to monitor electrical activity of a heart and implantable pulse generators (IPGs), such as pacemakers, leadless pacemakers, and implantable cardioverter defibrillators (ICDs) used in the treatment of cardiac conditions, and neuromodulators or neurostimulators used in chronic pain management or the actuation and control of other body systems.

IEDs have traditionally used hard metal cases, lids, and glass to metal seal (GTMS) feedthrus to contain a battery stack. The cases are connected to the internal chemical potential either directly when the anode is attached to the case, or indirectly if the electrolyte contacts the case. The closed assembly is then placed inside another metal can that contains the rest of the electronic components. This case inside a can assembly method adds packaging inefficiencies from the metal case and can. In addition, the battery internal geometry is constrained to flat planes.

Moreover, this can inside a case approach of a conventional IED battery is often of a configuration that creates "dead space" within the implantable medical device (e.g., a can having a substantially square or rectangular shape). Although a thoughtful design approach can help to reduce the amount of such dead space, an appreciable volume of space within the IED typically remains unusable when employing a conventional IED battery. Also, the metal battery case that contains the active battery components must be of a thickness sufficient to protect against battery leakage. The thickness of the battery case must also be taken into consideration when allocating space within the IED to house a battery source of a conventional design.

It is well appreciated in the IED manufacturing industry that the battery component of an IED requires the allocation of an appreciable percentage of usable space within the IED and significantly impacts the physical configuration of the IED. It can, therefore, be appreciated that reducing the size of the battery is a desirable design objective. However, reducing IED battery size results in a corresponding reduction in battery capacity. A reduction in capacity limits the duration of service time within the patient before battery replacement is required. Battery replacement in many cases requires surgical replacement of the entire device. Thus, there are limits on the ability to make significant battery size reductions using conventional IED battery design principles.

An ICM device may record cardiac activity of a patient over time and report such cardiac activity to an external device. The ICM device may optionally perform various levels of sophisticated analysis of the cardiac activity and based thereon perform additional recording operations. In general, an ICM include a battery, memory and electronic circuitry that are hermetically sealed within a metal housing (generally referred to as the "can"). The metal housing typically is formed of titanium and includes a shell (e.g., opposed concave half shells that are welded together, a "deep drawn shell, etc.) to form a device housing with an interconnect cavity, in which the battery, memory, pulse generator and/or processor module reside. The half shells have an oval contour with a header receptacle area configured to receive a header assembly. A feed-through assembly is located at the header receptacle area and is sealed to the device housing to form an interface for conductors to enter/exit the interconnect cavity.

Most medical devices use sensor terminals isolated in leads or polymer headers to detect bio-electric signals. However, in an ICM, the device housing ("can") may be used as a biosense electrode, and the same device can is used as the battery case, which is in contact with the electrochemical potentials of the battery. Because of this contact between the battery and the case, the housing becomes negative, i.e., case negative. In this way, the electrochemical potentials of the battery may introduce noise, negatively affecting biosensing of the ICM.

There is a need in the implantable electronic device manufacturing community for an IED battery implementation which provides for an overall flexibility in IED battery size, shape and form factor, without a corresponding reduction in battery capacity, and without imposing safety concerns that would render the medical device unsuitable for use. There is further a need for an ICM with an improved signal-to-noise ratio. The present invention fulfills these and other needs.

BRIEF SUMMARY OF THE INVENTION

In certain aspects, a battery for use in an implantable electronic device is provided. In one embodiment, the battery comprises a pouch-type battery enclosure having an internal surface and an external surface, and a cathode, an anode, and electrolyte disposed within the internal surface of the pouch-type enclosure. The battery may have greater than 20 megaohms of isolation between the anode and the external surface of the pouch-type battery enclosure and the cathode and the external surface of the pouch-type battery enclosure.

In certain embodiments, the pouch-type battery enclosure has a contoured shape.

In certain embodiments, the pouch-type battery enclosure has a contoured shape, and the cathode is a variable thickness cathode that is contoured in shape so as to at least partially provide the contoured shape of the pouch-type enclosure.

In certain embodiments, the pouch-type battery enclosure has a contoured shape, and the anode is a variable thickness anode that is contoured in shape so as to at least partially provide the contoured shape of the pouch-type enclosure.

In certain embodiments, the pouch-type battery enclosure has a contoured shape, and the cathode and anode have variable thicknesses that are contoured in shape so as to at least partially provide the contoured shape of the pouch-type enclosure.

In certain embodiments, an electrolyte is provided in a reservoir that is disposed within the pouch-type battery enclosure. In certain embodiments, the electrolyte comprises gamma-butyrolactone (GbL).

In certain embodiments, the pouch-type battery enclosure has a contoured shape, and the electrolyte reservoir is contoured in shape so as to at least partially provide the contoured shape of the pouch-type enclosure.

In certain embodiments, the pouch-type enclosure is comprised of a polymer-metal laminate.

In certain embodiments, the polymer-metal laminate is a laminate of aluminum between polymer layers selected from the group consisting of: polypropylene, polyethylene, polyamide, polybutylene-terephthalate and polyethylene-terephthalate.

In certain embodiments, an implantable electronic device, comprising: a header assembly and a housing, the housing comprising an electronics and a battery, the battery comprising a pouch-type battery enclosure having an internal surface and an external surface, a cathode, an anode, and an electrolyte disposed within the internal surface of the pouch-type enclosure, is provided. In embodiments, the battery has greater than 20 megaohms of isolation between the anode and the external surface of the pouch-type battery enclosure and the cathode and the external surface of the pouch-type battery enclosure.

In certain embodiments, the device is an implantable cardiac monitor. In embodiments, the electrolyte is provided in a reservoir that is disposed within the pouch-type battery enclosure, the electrolyte comprises lithium salt with gamma-butyrolactone (GbL) as the primary electrolyte solvent.

In certain embodiments, the device is a pacemaker, and the electrolyte comprises lithium salt with gamma-butyrolactone (GbL) as the primary electrolyte solvent.

In some embodiments, the electrolyte may be provided in a reservoir, e.g., a void provided with structural support to hold electrolyte, a sponge or similar material to hold electrolyte, or other suitable system to contain electrolyte. In some embodiments, the electrolyte is selected such as not to outgas upon discharge of the battery. In come embodiments, the electrolyte comprises gamma-butyrolactone (GbL) or GbL/dimethoxyethane (DME).

In certain embodiments, the variable thickness cathode, the electrolyte reservoir, or a combination thereof provide the contoured shape of the pouch-type enclosure.

In other aspects, disclosed herein is an implantable electronic device. In one embodiment, the device includes header assembly and a housing, wherein the housing comprises an electronic hybrid and a battery. The battery may include a pouch-type enclosure with a contoured shape, including a cathode, anode, and electrolyte disposed within the pouch-type enclosure.

The implantable electronic device may be an implantable cardiac monitor or implantable pulse generator.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

Although the following figures and description illustrate specific embodiments and examples, the skilled artisan will appreciate that various changes and modifications may be made without departing from the spirit and scope of the disclosure.

FIG. 3A is a side cross-section view of an embodiment of a housing including a pouch-type battery of the disclosure with a variable height cathode disposed within the housing.

FIG. 3B is an exploded view of a portion of FIG. 3A.

Additional embodiments and features are set forth in part in the description that follows, and will become apparent to those skilled in the art upon reading of the specification. A further understanding of the nature and advantages of the present disclosure can be realized by reference to the remaining portions of the specification and the drawings, which forms a part of this disclosure.

DETAILED DESCRIPTION

Reference will now be made in detail to representative embodiments described herein and illustrated in the accompanying drawings. It should be understood that the following descriptions are not intended to limit the disclosure to one preferred embodiment. To the contrary, it is intended to cover alternatives, modifications, and equivalents as can be included within the spirit and scope of the described embodiments as defined by the appended claims.

Implementations of the present disclosure generally relate to an implantable electronic device (IED), such as an implantable cardiac monitor (ICM) or an implantable pulse generator (IPG) and to batteries for use in connection with such devices. However, the IED of the disclosure may be of any form and function known in the art, and is not limited to those disclosed herein.

Figure 1A:
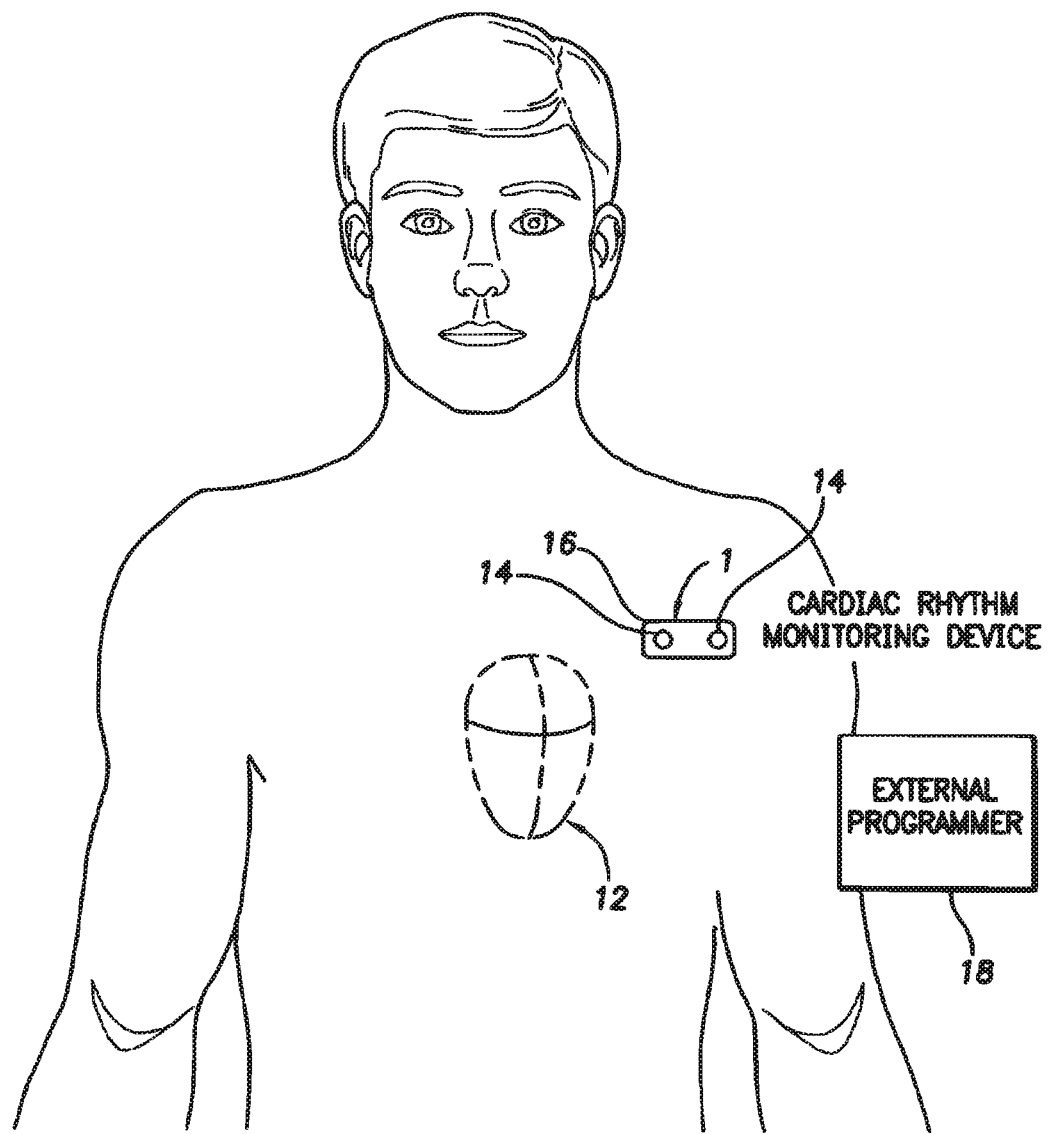
FIG. 1A illustrates an implantable cardiac monitoring (ICM) device intended for subcutaneous implantation at a site near the heart in accordance with embodiments herein.

Referring now to the drawings and particularly to FIG. 1A, there is shown an implantable cardiac monitoring device (ICM) 1 intended for subcutaneous implantation at a site near the heart 12. ICM 1 monitors electrical signals and does not administer therapy. The ICM 1 includes a pair of spaced-apart sense electrodes 14 positioned with respect to a housing 16. The sense electrodes 14 provide for detection of far field electrogram signals. Numerous configurations of electrode arrangements are possible. For example, the electrodes 14 may be located on the same side of the housing 16. Alternatively, the electrodes 14 may be located on opposite sides of the housing 16. One of the electrodes 14 may be formed as part of the housing 16, for example, by coating all but a portion of the housing with a nonconductive material such that the uncoated portion forms the electrode. In this case, the other of the electrodes 14 may be electrically isolated from the housing electrode by placing it on a component separate from the housing, such as a header (not shown).

The housing 16 includes various other components such as: sense electronics for receiving signals from the electrodes, a microprocessor for processing the signals in accordance with algorithms, such as the AF detection algorithm described herein, a loop memory for temporary storage of electrograms, a device memory for long-term storage of electrograms upon certain triggering events, such as AF detection, sensors for detecting patient activity and a battery for powering components.

The monitoring device 1 senses far field electrograms; processes the electrograms to detect arrhythmias and if an arrhythmia is detected; automatically records the electrograms in memory for subsequent transmission to an external device 18. Electrogram processing and arrhythmia detection is provided for, at least in part, by algorithms embodied in the microprocessor. In one configuration, the monitoring device is operative to detect atrial fibrillation.

In accordance with embodiments of this disclosure, housing 16 is used as a biosense electrode 14. As described in greater detail below, in accordance with certain embodiments, the battery of the ICM 1 is sealed in a laminar pouch such that the electrochemical potential of the battery chemistry is removed from the sensing case 16. In certain embodiments having a pouch-type enclosure provides 20 megaohms (MΩ) of isolation between the anode and the external surface of the pouch-type battery enclosure and the cathode and the external surface of the pouch-type battery enclosure. The pouch of the battery isolates the battery chemistry from housing 16, such that housing 16 is neutral, i.e., ICM 1 is case neutral. In accordance with embodiments, electrolyte is isolated from housing 16 by the pouch, such that electrolyte is not in contact with the case during operation of the device. Advantageously, since housing 16 is not in contact with the electrochemical potentials of the battery, the signal-to-noise ratio may be greatly improved, thus improving the accuracy of data gathered by ICM 1.

In addition, as described herein, the pouch of the battery removes the battery case's packaging inefficiencies, and eliminated the requirement of a glass to metal seal, greatly impacting the size of the ICM.

In an embodiment, ICM 1 has a battery comprising a lithium anode and a cathode comprising petroleum coke CFx/SVO.

In accordance with embodiments of this disclosure, since the pouch cell cannot hold as much pressure as a metallic case, a battery chemistry is selected such that it does not outgas when discharged. An electrolyte comprising gamma-butyrolactone (GbL) or GbL/dimethoxyethane (DME) can be selected. In certain embodiments, the battery is activated with an electrolyte of 1M $LiBF_4$ in gamma-butyrolactone (GbL) or 1M $LiBF_4$ in a 50/50 mixture, by volume, of GbL/DME. In certain embodiments the CFx comprises non-fibrous fluorinated carbon made from a petroleum coke material. As used herein, CFx has an empirical formula $(CF_x)_n$ where $0 < x < 1.25$.

Certain embodiments of the current invention provide for an improved IPG. Certain embodiments of IPGs administer electrotherapy or other neurostimulation via an implantable lead having a lead connector end on a proximal end of the implantable lead. The IPG includes a housing or can and a connector assembly enclosed in a header to form a header connector assembly that is coupled to the housing or can. The header connector assembly has at least one lead connector receiving bore or receptacle that includes electrical contacts of the connector assembly that make electrical contact with corresponding electrical terminals on the lead connector end on the proximal end of the implantable lead when the lead connector end is plugged into or otherwise received in the lead connector receiving bore or receptacle.

Via the electrical connection between the corresponding electrical terminals of the lead connector end and the electrical contacts of the lead connector receiving bore, electrical signals can be administered from the IPG and through the lead to patient tissue. Similarly, but in reverse, electrical signals originating in patient tissue can travel via the lead to the IPG to be sensed at the IPG.

Certain embodiments provide for an improved subcutaneous ICD. Subcutaneous ICDs do not use endocardial, transvenous or epicardial lead wires, and deliver defibrillation using subcutaneous electrodes.

Certain embodiments provide for an improved IPGs operating without a lead, such as a leadless pacemaker. Leadless pacemakers comprises at least two leadless electrodes configured for delivering cardiac pacing pulses, sensing evoked and/or natural cardiac electrical signals.

Figure 1B:
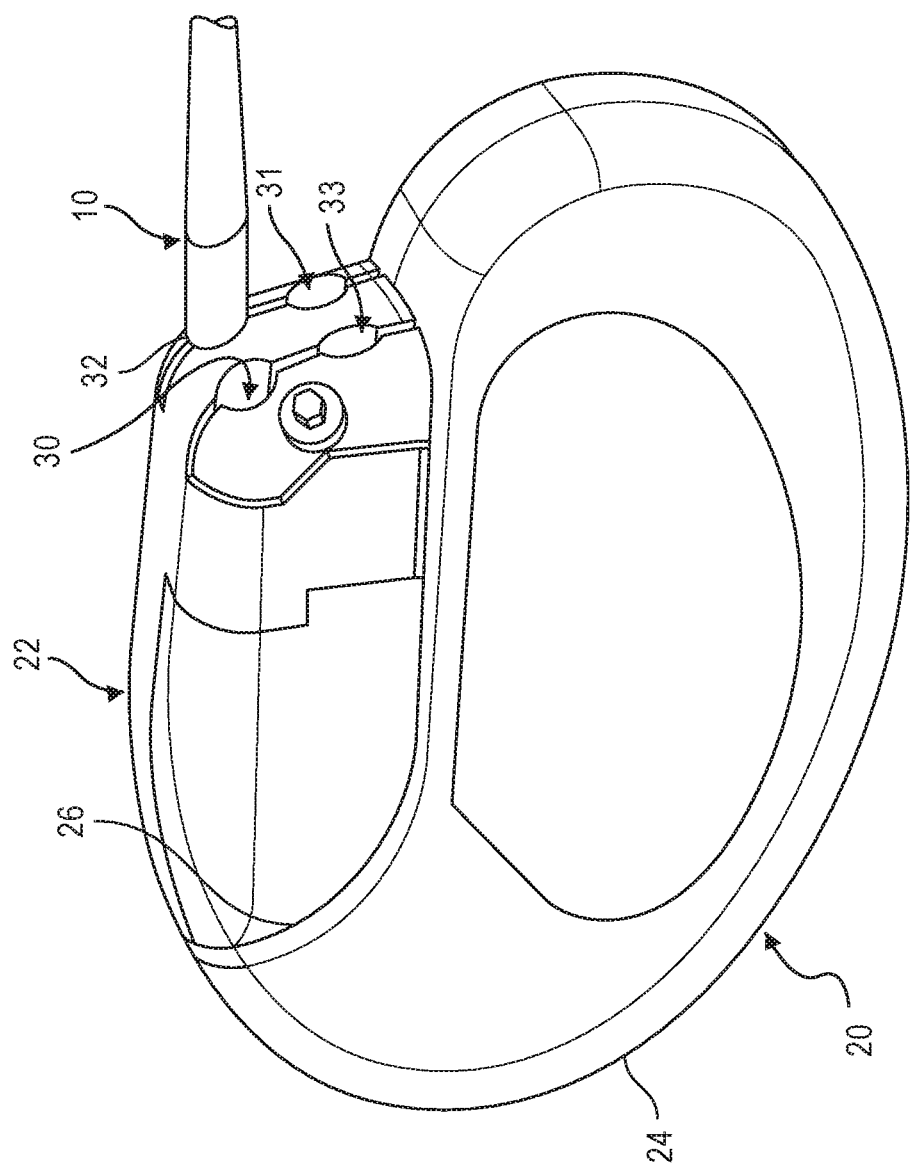
FIG. 1B is an isometric view of an exemplary cardiac pacemaker/defibrillator unit (i.e., implantable pulse generator (IPG)) that may be used in connection with an embodiment of a housing including a pouch-type battery of the disclosure.

By way of non-limiting example, FIG. 1B shows a multi-site or multi-chamber cardiac pacemaker/defibrillator unit that is generally representative of any type of IPG 20. IPG 20 incorporates a header assembly 22 coupled to a housing 24. The IPG 20 is of a conventional design, including a hermetically sealed housing 24, which is also known as a can or casing. The housing 24 encloses the electronic components (e.g., battery, hybrid electronics, etc.) of the IPG 20 with the header assembly 22 mounted along a top surface 26 of the housing 24. As described in further detail herein, the housing 24 may include a pouch-type battery of the disclosure.

FIG. 1B illustrates that, in some embodiments, the header assembly 22 may include four or more lead connector receiving bores or receptacles 30, 31, 32 and 33 for receiving the lead connector ends of four implantable leads. FIG. 1B also shows the proximal end portion 10 of a lead, wherein the lead connector end on the proximal end portion 10 of the lead is received in a corresponding receptacle 32. In other embodiments, the header assembly 22 includes two receptacles comprising a single pair of receptacles (i.e., receptacles 30 and 33) for receiving the proximal ends of leads such as, for example, conventional bipolar leads and/or conventional cardioverting and/or defibrillating leads. In this regard, in some embodiments, the IPG includes one or more implantable medical leads configured to electrically couple with the implantable pulse generator.

The IPG illustrated in FIG. 1B is intended as an example of an implantable electronic device useful in connection with the pouch-type battery disclosed herein. However, as understood by those of skill in the art, the pouch-type battery may be used with any suitable implantable electronic device and integrated into any housing or casing configuration known in the art.

The implantable electronic device configurations, batteries, and methods disclosed herein are advantageous for at least the reason that they provide improved device packaging efficiency and device longevity. Electronic hybrids used in implantable electronic devices are typically comprised of tall and short electronic components. Traditionally, battery size is dictated by the tallest component on the hybrid and the rigid form of the can housing. However, in accordance with the present disclosure, it has been found that implantable electronic device efficiency and longevity can be improved by making use of the space around the tall and short components of the electronic hybrid as described herein. In this regard, it has been found that the improved battery designs provided herein can improve battery and implantable electronic device longevity by up to 20%, as compared to traditional designs.

Certain aspects of the disclosure relate to a battery for use in an implantable electronic devices described herein. In one embodiment, the battery may include a pouch-type enclosure constructed in accordance with the teaching of U.S. Publication Nos. 2007/0154794, 2012/0040235, and U.S. Pat. No. 6,042,966, each of which is incorporated herein by reference in their entirety.

Figure 2:
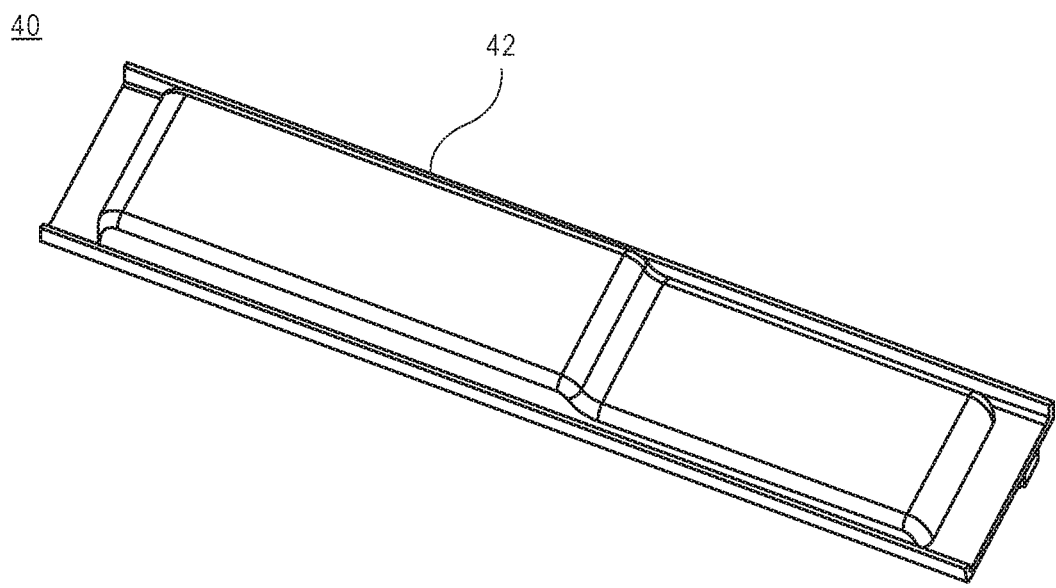
FIG. 2 is an isometric top view of a pouch-type battery enclosure illustrating an exemplary contoured shape.

In certain embodiments, the battery may include a pouch-type enclosure with a contoured shape. FIG. 2 illustrates a battery system 40 having pouch-type battery enclosure 42 with an exemplary contoured shape. In certain embodiments pouch-type battery enclosure 42 does not have a contoured shape. In certain embodiments pouch-type battery enclosure 42 provides 20 megaohms (MΩ) of isolation between the anode and the external surface of the pouch-type battery enclosure and the cathode and the external surface of the pouch-type battery enclosure. Without intending to be limited, the shape of the pouch-type enclosure may generally be contoured to conform to the space around components of an electronic hybrid of various dimensions, e.g. tall and short, of an implantable electronic device (not shown). By way of non-limiting example, such configurations are generally illustrated in FIGS. 3A-3B, 4, and 5 as discussed in further detail below.

In certain embodiments, the battery may further include a cathode, anode, separator assembly, and electrolyte disposed within the pouch-type enclosure. With reference to FIG. 3A, battery system 40 is illustrated with a shape generally contoured to conform to the shape of the tall 50A and short 50B components of electronic hybrid 50, both located together in housing 24. Housing 24 may also include a feed-thru assembly 60 for connecting housing 24 to an implantable electronic device header assembly, e.g., header assembly 22 (not shown).

FIG. 3B shows an enlarged view of a portion of FIG. 3A. As shown in FIG. 3B, battery system 40 may include cathode 44, anode 45 and electrolyte 46 disposed within the pouch-type enclosure 42. The battery system 40 may also include current collection materials (Ni, Ti, etc.) and separator assembly materials (microporous, inert materials such as polyethylene, polypropylene, etc.), as generally known in the art (not shown).

In certain embodiments, the cathode may have a generally flat or planar shape, or the cathode may a contoured shape. In certain embodiments, the cathode may be a variable thickness cathode. In certain aspects, the cathode (flat, contoured, variable thickness, etc.) may provide, at least in part, the contoured shape of the pouch-type battery. In certain embodiments, the shape of the cathode, e.g., the variable thickness cathode, may be contoured to conform to the space around the tall and short components of an electronic hybrid of an implantable electronic device, to thereby maximize use of space within the housing.

In accordance with certain aspects of the disclosure, the provision of a pouch-type battery with a contoured shape and the use of a cathode within such a pouch-type battery, e.g., a variable thickness cathode, to conform to the space around the tall and short components of an electronic hybrid of an implantable electronic device, thereby maximizing battery efficiencies and increasing device longevity. Without intending to be limited by theory, by utilizing the space created around electronic hybrid components of differing heights and maximizing use of volumetric space around electronic hybrid components, battery packaging efficiencies and device longevity can be increased by up to 20-30%, as compared to traditional battery designs.

Any suitable battery chemistry system known in the art for implantable electronic devices may be used in connection with the present disclosure. Such battery systems have been developed and are generally recognized by those of skill in the art. By way of example, primary battery systems typically utilize lithium metal anodes with cathode systems including, e.g., iodine, iodine-polyvinylpyridine ($I_2$-PVP), manganese dioxide ($MnO_2$), carbon monofluoride (polycarbon monofluoride or CFx), silver vanadium oxide (SVO) and hybrid cathodes (e.g., CFx-SVO hybrids), etc. By way of non-limiting example, systems may include iodine, iodine-polyvinylpyrindine ($I_2$-PVP), manganese dioxide ($MnO_2$), carbon monofluoride (CFx), silver vanadium oxide (SVO), copper silver vanadium oxide (CSVO), cobalt oxide, nickel oxide, fluorinated carbon, copper oxide, copper sulfide, iron sulfide, iron disulfide, titanium disulfide, copper vanadium oxide, and hybrids (e.g., CFx-SVO hybrids) and mixtures thereof.

Secondary lithium ion batteries have also been developed for medical applications where the batteries may be recharged while remaining implanted. Rechargeable battery systems typically include a carbonaceous anode, and a metal oxide cathode, with both electrode materials having the ability to intercalate lithium ions reversibly. Typical carbonaceous anode materials may include graphite, carbon black, coke, petroleum coke, and mesophase carbon microbeads (MCMB), etc. Typical cathode materials may include nickel, manganese, cobalt, and titanium based oxides, such as nickel manganese cobalt oxide (NMC), lithium cobalt oxide ($LiCoO_2$), lithium nickel oxide ($LiNiO_2$), lithium manganese oxide ($LiMnO_2$), lithium iron phosphate ($LiFePO_4$), lithium titanate oxide ($Li_2TiO_3$), etc.

Any suitable electrolyte material known in the art for implantable electronic devices may be used in connection with the pouch-type batteries of the disclosure, selected for compatibility with the appropriate anode and cathode materials. By way of non-limiting example, exemplary electrolyte may comprise an inorganic alkali metal salt, and in the case of an anode comprising lithium, the alkali metal salt of the electrolyte may be a lithium based salt. Known lithium salts that are useful as a vehicle for transport of alkali metal ions from the anode to the cathode include $LiPF_6$, $LiBF_4$, $LiAsF_6$, $LiSbF_6$, $LiClO_4$, $LiAlCl_4$, $LiGaCl_4$, $LiC(SO_2CF_3)_3$, $LiN(SO_2CF_3)_2$, LiSCN, $LiO_3SCF_2CF_3$, $LiC_6F_5SO_3$, $LiO_2CF_3$, $LiSO_3F$, $LiB(C_6H_5)_4$ and $LiCF_3SO_3$, and mixtures thereof. Suitable salt concentrations typically range between about 0.8 to 1.5 molar. Optional additives and solvents may be added to the electrolyte, as is generally known in the art. In an embodiment, the electrolyte is selected such that the battery it does not outgas when the battery is discharged as described herein.

By way of non-limiting example, lithium/iodine-polyvinylpyridine (Li/$I_2$-PVP) systems may be used in applications requiring a current in the microampere range (e.g., implantable cardiac pacemakers). An alternative option for implantable electronic devices requiring current outputs in the milliampere range is the lithium/carbon monofluoride (Li/CFx) system. Lithium/manganese dioxide (Li/$MnO_2$) battery systems may be used in medium-range applications requiring a current in the milliwatt range (e.g., neurostimulators, drug delivery systems, and pacemakers with additional functionality).

In certain embodiments, hybrid battery systems using carbon monofluoride ($CF_x$) and silver vanadium oxide (SVO) are used to obtain medium range current outputs, suitable with e.g., pacemakers and leadless pacemakers. Lithium/silver vanadium oxide (Li/SVO) systems and lithium/manganese dioxide (Li/MnO₂) systems may be used in applications with high current demands (e.g., implantable cardioverter defibrillators).

In certain embodiments, an electrolyte is provided in a reservoir that is disposed within the pouch-type enclosure. The electrolyte may be isolated from the housing of the device using the pouch-type enclosure, such that there are 20 megaohms (MΩ) of isolation between the anode and the external surface of the pouch-type battery enclosure and the cathode and the external surface of the pouch-type battery enclosure.

In certain embodiments, the anode is a lithium metal anode, and the cathode is formed from carbon monofluoride (CFx)-silver vanadium oxide (SVO) hybrid, wherein the CFx comprises a non-fibrous fluorinated carbon made from a petroleum coke material, having an empirical formula $(CF_x)_n$ where 0<x<1.25. In certain embodiments, wherein the cell is activated with 1M LiBF₄ in gamma-butyrolactone (GbL) or wherein cell is activated with an electrolyte of 1M LiBF₄ in a 50/50 mixture, by volume, of GbL/DME (glyme or 1,2-dimethoxyethane or ethylene glycol dimethyl ether). Since a pouch cell cannot hold as much pressure as a metallic case, the cell chemistry may be selected such that the battery does not outgas when discharged. An electrolyte comprising GbL or GbL/DME may be selected for this reason.

In accordance with certain aspects of the disclosure, any suitable method for forming the contoured shape of the variable thickness cathode may be used. In one embodiment, the variable thickness cathode may be formed from granulated powder of the cathode material. By way of example, the granulated powder may be die cast into a contoured form to fit a desired shape within the pouch-type enclosure. Alternatively, the variable thickness cathode may be formed by extrusion, sheeting or casting, or screen printing. Exemplary methods are discussion in further detail below.

By way on non-limiting example, in certain embodiments, the variable thickness cathodes of the disclosure may be formed using die cast/pressed powder methods. For instance, the active cathode material (as described above), as well as optional inactive materials, such as graphite and carbon black, may be mixed with a binder. The cathode materials may optionally be screened to reduce particle size. In certain embodiments, the cathode screen may be an open mesh of 40-90% open. The mesh may be expanded metal, stamped, or photoetched made from, e.g., aluminum, titanium, copper, or stainless depending on cathode chemistry. Any suitable binder may be used, e.g., fluoropolymers such as polytetrafluoroethylene (PTFE), polyolefins, etc. The mixing process may comprise wet mixing with a solvent such as isopar or alcohol in a blender or equivalent in order to disperse the powder comprising the cathode material and initiate binder fibrillation. Once the powder and binder are mixed, the mixture is dried to form a cake. The dried cake is then pelletized or granulated. The granulated powder can then be poured into a cavity matching the desired contoured variable thickness cathode shape and compacted. In another embodiment, the dry cathode/inactive materials may be mixed with binder, the mixture may be extruded to initiate fibrillation, and the resulting mixture may be granulated so it can be poured into a die and compacted.

In other embodiments, the variable thickness cathode of the disclosure may be formed using an extrusion process. For instance, the cathode material may be mixed with a binder and granulated, as generally described above. The granulated cathode material may then be ram extruded through a profiled slot die to make a profiled cathode ribbon. The ribbon can then be cut into the correct sections per weight, and compacted in die to form the desired contoured variable thickness cathode shape. Again, the cathode materials may optionally be screened to reduce particle size. In certain embodiments, the cathode screen may be an open mesh of 40-90% open. The mesh may be expanded metal, stamped, or photoetched made from, e.g., aluminum, titanium, copper, or stainless depending on cathode chemistry.

In other embodiments, the variable thickness cathode of the disclosure may be formed using a sheeting or casting process. For instance, the cathode materials may be mixed with a binder as generally described above, except a liquid binder such as polyvinylidene fluoride in N-methylpyrrolidine (PVDF in NMP) or NMP is used in place of PTFE. The dry ingredients plus the liquid binder may be mixed into a slurry, poured into a cathode mold, and cured. In certain embodiment, the solvent content for the mixing process may be, e.g., 30%-80% solvent. The casting solvent content may be, e.g., 10%-30%. A solid cathode current collector is also acceptable.

In other embodiments, the variable thickness cathode of the disclosure may be formed using a screen printing process. By way of example, a binding material may be prepared by solubilizing a desired binder in a polar solvent and heating the solution under vacuum with agitation to form a homogeneous liquid binder. A mixture of fine powdered carbon and cathode material (as described herein), may then be mixed with the binding material to form a homogenous ink, slurry or paste depending on viscosity. This slurry/paste is deposited on a screen mask with a conductive substrate underneath, and the slurry/paste is bladed or squeegeed onto the conductive substrate. The printed conductor is then dried to remove any remaining polar solvent, leaving behind a deposited cathode material. Without intending to be limited, an advantage of screen printing is the cathodes can be produced in any shape, orientation, or depth of porosity. With this design flexibility, variable thickness cathodes in accordance with the disclosure may be produced to occupy the void spaces around circuit and electronic components. This ability leads to smaller devices and higher levels of stored energy within devices to, e.g., increase device longevity, improve device sensitivity or performance, or enable other capabilities such as wireless communication protocols, electromechanical actuators, etc.

In another aspect of the disclosure, the space around the electronic hybrid components can be used for electrolyte. Primary lithium chemistry battery systems absorb electrolyte as the cell discharges. These chemistries are traditionally filled so the cell is very wet at beginning of life, thus requiring free space to be available within the battery for electrolyte. Traditional metal cases force the internal stack (cathode/anode stack) assembly to fill less of the internal volume of the battery enclosure so as to provide free space for electrolyte. In accordance with aspects of the disclosure, a contoured, pouch-type enclosure provides additional space for electrolyte material, as compared to traditional battery designs.

In certain embodiments, the contoured, pouch-type enclosure may include a reservoir space configured to hold electrolyte material. As described herein, the reservoir may be incorporated into the shape of the pouch-type enclosure that is contoured to conform to the space around components of variable heights of an electronic hybrid of an implantable electronic device, e.g., the tall and short components. In certain embodiments, the reservoir may include a void, cup, sponge, or other suitable structural component configured to hold electrolyte solution.

In certain embodiments, the reservoir configured to hold electrolyte material may be sized and shaped to conform to the space around the tall and short components of an electronic hybrid of an implantable electronic device to thereby maximize the volume of electrolyte material available to the implantable electronic device.

Figure 4:
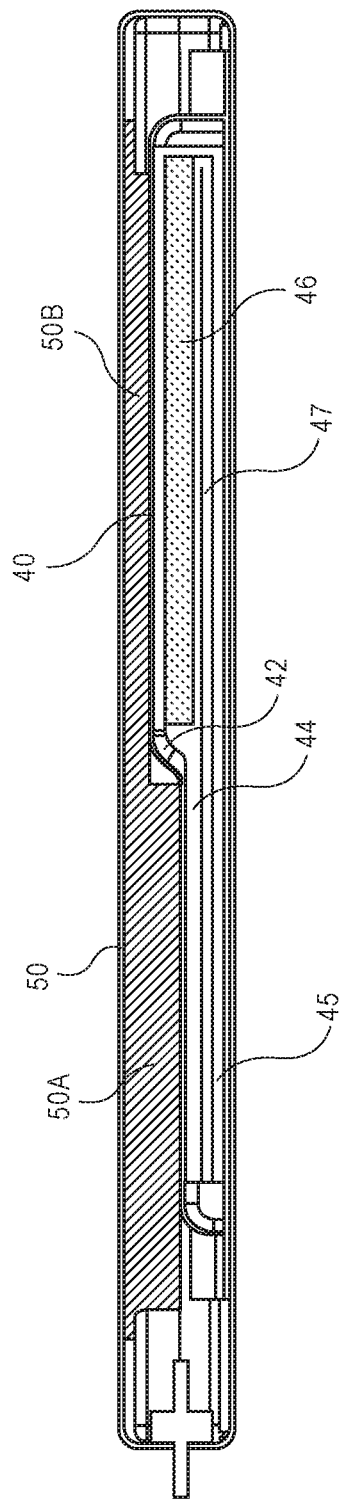
FIG. 4 is a side cross-section view of an embodiment of a housing including a pouch-type battery of the disclosure with an electrolyte reservoir within the housing.

For instance, with reference to FIG. 4, battery system 40 may include cathode 44, anode 45 and reservoir 47 with electrolyte 46 disposed within the pouch-type enclosure 42. The cathode 44 and/or anode 45 may provide the contoured shape of the pouch-type enclosure 42. Battery system 40 is illustrated with a shape generally contoured to conform to the shape of the tall 50A and short 50B components of electronic hybrid 50. As illustrated, reservoir 47 is sized and shaped to conform to the space around tall 50A and short 50B components of electronic hybrid 50, to thereby maximize the volume of electrolyte 46 material available.

Figure 5:
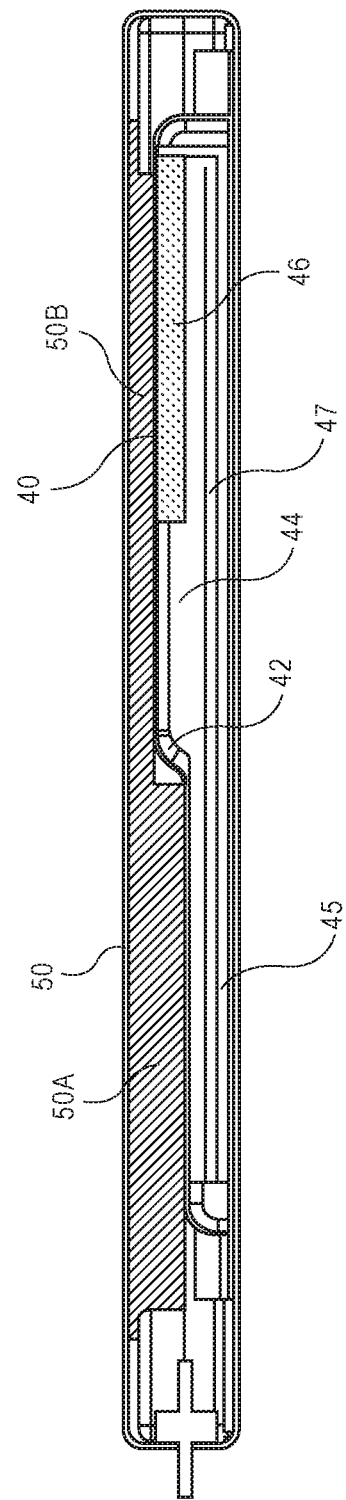
FIG. 5 is a side cross-section view of an embodiment of a housing including a pouch-type battery of the disclosure with an electrolyte reservoir and variable height cathode disposed within the housing.

In other embodiments, the reservoir configured to hold electrolyte may be used together with a variable height cathode. With reference to FIG. 5, battery system 40 may include cathode 44, anode 45 and reservoir 47 with electrolyte 46 disposed within the pouch-type enclosure 42. The cathode 44 and/or anode 45 may provide the contoured shape of the pouch-type enclosure 42. Battery system 40 is illustrated with a shape generally contoured to conform to the shape of electronic components having different heights, e.g., the tall 50A and short 50B components of electronic hybrid 50. As illustrated, variable height cathode 44 is sized and shaped to conform to the tall 50A and short 50B components of electronic hybrid 50, and variable height cathode 44 and reservoir 47 both are present in the space around tall 50A and short 50B components of electronic hybrid 50, thereby maximizing use of this space for a dual purpose.

In certain embodiments, the pouch-type enclosure may be a laminate formed of a flexible material, such as a metal-polymer laminate. By way of non-limiting example, the pouch material may be formed from a polymer-metal laminate such as aluminum between two polymer layers. The polymer layers may be selected from polypropylene, polyethylene, polyamide, polybutylene-terephthalate or polyethylene-terephthalate. For instance, an inner layer may be selected from polypropylene or polyethylene, and an outer layer may be selected from polyamide, polybutylene-terephthalate or polyethylene-terephthalate. In one embodiment, the pouch-type enclosure may be formed from a laminate selected from polypropylene-aluminum-polyamide, polyethylene-aluminum-polybutylene-terephthalate, ionomer resin, or polyethylene-aluminum-polyethylene-terephthalate.

The pouch-type enclosure may be formed in any suitable manner known in the art, e.g., using heat and vacuum. By way of non-limiting example, the pouch may be sealed using a resistive band heat source, ultrasonic welding, laser welding, or thermal welding of the edges of the pouch, during which welding the inner and outer polymer layers are joined together. The cathode, anode, and any current collector and separator assembly can be placed into the pouch bag. A cathode tab extends from the cathode(s) and an anode tab extends from the anode(s) in order to connect the battery to an external circuit outside the pouch. In order to seal the pouch, a polymer or other material used in forming the pouch, e.g., polypropylene, polyethylene, polyamide, polybutylene-terephthalate, ionomer resin, or polyethylene-terephthalate, may be added to the surface of the pouch on either side of the tabs to reinforce the bonding between the polymer membrane inside the pouch and the cathode and anode tabs. Insulating tape may also be used to prevent a short circuit between the cathode and anode tabs and pouch prior to or after thermally sealing the pouch to the tabs. The battery may then be placed into the device housing without a hard battery housing.

In certain embodiments, the pouch bag may be partially sealed, if desired. At that point the pouch bag may be filled with electrolyte, and fully sealed, e.g., heat sealed, to enclose the pouch while permitting the cathode and anode tabs to extend past the borders of the pouch. In certain embodiments, the pouch bag may be sealed using thermal welding, e.g., using electric resistance heating. The contours of the pouch may be utilized for cathode, anode, or electrolyte to maximize battery and device packaging efficiency. As understood by those of skill in the art, the order and sequence of layering, sealing and filling may be modified and the disclosure is not so limited. Without intending to be limited, the thermoplastic polymer weld may serve to block diffusion of water and air from the outside, as well as to act as a barrier for the electrolyte within the battery enclosure.

In other aspects, the battery designs of the disclosure can provide improved sensitivity and accuracy in operation of implantable electronic devices. In certain embodiments, the pouch-type enclosure of the battery allows the housing enclosing the battery to be used as an efficient sense electrode without a bias voltage overlaid on the sensing voltage of the battery. This allows the device to be more sensitive and accurate when detecting electro physiological signals. Without intending to be limited, when a metal battery case is used as a sense electrode—battery voltage changes with loading conditions, thereby increasing signal processing difficulties. However, in accordance with the present disclosure, a pouch-type battery enclosure removes the battery case from the sensing circuit, thereby simplifying signal processing, as well as increasing packaging efficiency.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed:

1. A battery for an implantable electronic device, comprising:
   a pouch-type battery enclosure having an internal surface and an external surface; and
   electrodes that include an anode and a cathode, the electrodes and an electrolyte being disposed within the internal surface of the pouch-type enclosure, wherein the battery has greater than 20 megaohms of isolation between the anode and the external surface of the pouch-type battery enclosure and the cathode and the external surface of the pouch-type battery enclosure, and a first one of the electrodes having different regions that concurrently have a different thickness, the thickness of each of the different regions being constant within the region.

2. The battery of claim 1, wherein the pouch-type enclosure is comprised of a polymer-metal laminate.

3. The battery of claim 2, wherein the polymer-metal laminate is a laminate of aluminum between polymer layers selected from the group consisting of: polypropylene, polyethylene, polyamide, polybutylene-terephthalate, iononer resin, and polyethylene-terephthalate.

4. An implantable electronic device, comprising:
a header assembly and a housing;
the housing comprising an electronics and a battery, the battery comprising a pouch-type battery enclosure having an internal surface and an external surface; and
electrodes that include an anode and a cathode, the electrodes and an electrolyte being disposed within the internal surface of the pouch-type enclosure, wherein the battery has greater than 20 megaohms of isolation between the anode and the external surface of the pouch-type battery enclosure and between the cathode and the external surface of the pouch-type battery enclosure, and
a first one of the electrodes having different regions that concurrently have a different thickness, the thickness of each of the different regions being constant within the region.

5. The implantable electronic device of claim 4, wherein the device is selected from a group consisting of an implantable cardiac monitor and a pacemaker.

6. The battery of claim 1, wherein the battery excludes a glass-to-metal seal.

7. The battery of claim 1, wherein:
the first electrode has a first side and a second side arranged such that the first side is between the enclosure and the second side;
the internal surface of the enclosure is between the external surface of the enclosure and the first electrode;
the enclosure is positioned such that different portions of the external surface are each located over a different one of the electrode regions; and
the enclosure has a contour that conforms to the first side of the first electrode such that the different portions of the external surface are at different distances from second side of the first electrode.

8. The battery of claim 1, wherein a tab is connected to the first electrode.

9. The battery of claim 1, wherein the first electrode has a layer that includes active material and the layer has different regions that each has a different thickness.

10. The battery of claim 9, wherein:
the layer has a first side and a second side arranged such that the first side is between the enclosure and the second side;
the internal surface of the enclosure is between the external surface of the enclosure and the first electrode;
the enclosure is positioned such that different portions of the external surface are each located over a different one of the layer regions; and
the enclosure has a contour that conforms to the layer such that the different portions of the external surface are at different distances from second side of the layer.

11. The battery of claim 9, wherein a second one of the electrodes has a planar shape in that the second electrode has a constant thickness.

12. The implantable electronic device of claim 4, wherein the battery excludes a glass-to-metal seal.

13. The implantable electronic device of claim 4, wherein:
the first electrode has a first side and a second side arranged such that the first side is between the enclosure and the second side;
the internal surface of the enclosure is between the external surface of the enclosure and the first electrode;
the enclosure is positioned such that different portions of the external surface are each located over a different one of the electrode regions; and
the enclosure has a contour that conforms to the first side of the first electrode such that the different portions of the external surface are at different distances from second side of the first electrode.

14. The implantable electronic device of claim 13, wherein a tab is connected to the first electrode.

15. The implantable electronic device of claim 4, wherein the first electrode has a layer that includes active material and the layer has different regions that each has a different thickness.

16. The implantable electronic device of claim 15, wherein:
the layer has a first side and a second side arranged such that the first side is between the enclosure and the second side;
the internal surface of the enclosure is between the external surface of the enclosure and the first electrode;
the enclosure is positioned such that different portions of the external surface are each located over a different one of the layer regions; and
the enclosure has a contour that conforms to the layer such that the different portions of the external surface are at different distances from second side of the layer.

17. The implantable electronic device of claim 15, wherein a second one of the electrodes has a planar shape in that the second electrode has a constant thickness.

18. The implantable electronic device of claim 4,
a first one of the regions has a thickness that is less than a thickness of a second one of the regions,
the first region is adjacent to the second region such that an interface between the first region and the second region defines a recess in a surface of the first electrode, and
a portion of the component is positioned between the first region and the housing and in an interior of the recess.

19. The implantable electronic device of claim 4, wherein the enclosure is a bag.

20. The battery of claim 7, wherein the enclosure is a bag.

* * * * *